United States Patent
Körner

(10) Patent No.: US 8,327,518 B2
(45) Date of Patent: Dec. 11, 2012

(54) METHOD FOR MANUFACTURING A BENDABLE TUBE

(75) Inventor: Eberhard Körner, Knittlingen (DE)

(73) Assignee: Richard Wolf GmbH, Knittlingen (DE)

( * ) Notice: Subject to any disclaimer, the term of this patent is extended or adjusted under 35 U.S.C. 154(b) by 337 days.

(21) Appl. No.: 12/756,339

(22) Filed: Apr. 8, 2010

(65) Prior Publication Data

US 2010/0287755 A1 Nov. 18, 2010

(30) Foreign Application Priority Data

Apr. 9, 2009 (DE) .................. 10 2009 017 175

(51) Int. Cl.
*B23P 17/00* (2006.01)
*B23P 19/04* (2006.01)
*A61B 1/00* (2006.01)

(52) U.S. Cl. ........... 29/527.1; 29/454; 29/423; 600/142; 600/141; 138/120

(58) Field of Classification Search ............. 29/454, 29/527.1, 423; 606/142, 141, 139; 604/525; 138/120; 174/86; 600/142, 141, 139
See application file for complete search history.

(56) References Cited

U.S. PATENT DOCUMENTS

| | | | |
|---|---|---|---|
| 2,515,366 A * | 7/1950 | Zublin | 464/19 |
| 3,260,069 A | 7/1966 | Neilson et al. | |
| 3,583,393 A * | 6/1971 | Takahashi | 600/142 |
| 4,651,718 A * | 3/1987 | Collins et al. | 600/142 |
| 5,178,129 A * | 1/1993 | Chikama et al. | 600/142 |
| 5,215,338 A * | 6/1993 | Kimura et al. | 285/154.2 |
| 5,448,989 A * | 9/1995 | Heckele | 600/142 |
| 5,749,828 A * | 5/1998 | Solomon et al. | 600/141 |
| 5,807,241 A * | 9/1998 | Heimberger | 600/142 |
| 6,364,828 B1 * | 4/2002 | Yeung et al. | 600/142 |
| 6,641,528 B2 * | 11/2003 | Torii | 600/142 |
| 6,656,195 B2 * | 12/2003 | Peters et al. | 606/159 |
| 7,766,821 B2 * | 8/2010 | Brunnen et al. | 600/142 |
| 7,780,716 B2 * | 8/2010 | Pappas | 623/1.11 |
| 7,794,489 B2 * | 9/2010 | Shumer et al. | 623/1.11 |
| 7,799,065 B2 * | 9/2010 | Pappas | 623/1.11 |
| 7,846,162 B2 * | 12/2010 | Nelson et al. | 606/62 |
| 7,942,875 B2 * | 5/2011 | Nelson et al. | 606/63 |

(Continued)

FOREIGN PATENT DOCUMENTS

DE 195 35 179 A1 3/1997

(Continued)

OTHER PUBLICATIONS

British Search Report issued on Jul. 20, 2010 in British Application No. GB1005789.1.

*Primary Examiner* — Essama Omgba
(74) *Attorney, Agent, or Firm* — Panitch Schwarze Belisario & Nadel LLP

(57) ABSTRACT

With a method for manufacturing a bendable tube, which is preferably envisaged for an endoscopic instrument, first a tube is separated into several tube sections in a manner such that adjacent tube sections engage into one another with a positive fit in the axis direction of the tube. After the separation of the tube into several tube sections, one envisages peripherally arranging means for providing a positive fit transversely to the axis direction of the tube, on the regions of the tube sections, which are situated in engagement with one another.

3 Claims, 7 Drawing Sheets

U.S. PATENT DOCUMENTS

| | | | |
|---|---|---|---|
| 8,114,144 B2* | 2/2012 | Chow et al. | 623/1.11 |
| 8,128,650 B2* | 3/2012 | Boebel et al. | 606/205 |
| 2005/0272978 A1* | 12/2005 | Brunnen et al. | 600/142 |
| 2007/0161860 A1* | 7/2007 | Hosoi et al. | 600/142 |
| 2008/0249364 A1* | 10/2008 | Korner | 600/141 |
| 2010/0010309 A1* | 1/2010 | Kitagawa | 600/142 |
| 2011/0071356 A1* | 3/2011 | Edwards | 600/142 |
| 2012/0012220 A1* | 1/2012 | Perry | 138/120 |
| 2012/0165608 A1* | 6/2012 | Banik et al. | 600/141 |

FOREIGN PATENT DOCUMENTS

| | | |
|---|---|---|
| DE | 296 23 452 U1 | 7/1998 |
| DE | 101 13 713 C1 | 12/2002 |
| DE | 10 2005 054 057 A1 | 6/2007 |
| EP | 0 626 604 A2 | 11/1994 |
| GB | 2143920 A * | 2/1985 |

* cited by examiner

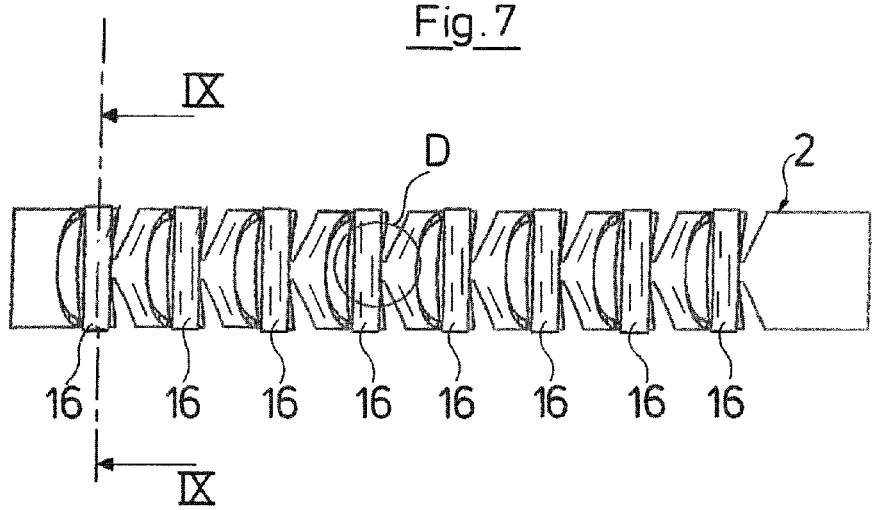
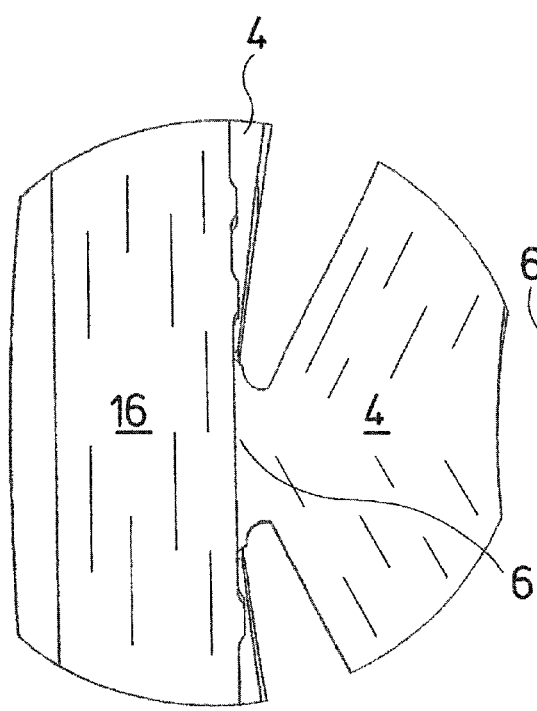

METHOD FOR MANUFACTURING A BENDABLE TUBE

BACKGROUND OF THE INVENTION

The invention relates to a method for manufacturing a bendable tube, in particular for an endoscopic instrument, in which a tube is separated into several tube sections in a manner such that adjacent tube sections engage into one another with a positive fit in the axis direction of the tube.

It is known to manufacture tubes of this type, in which several tube sections may be bent or are connected to one another in an articulated manner, by lugs formed on the tube sections engaging into recesses of adjacent tube sections, such that first individual tube sections are manufactured which are then manually joined together for forming a tube. This procedural method is comparatively time-consuming and costly, wherein the effort is yet further increased with an increasing number of the required tube sections, as well as with a reducing size of these tube sections. Moreover, bendable tubes manufactured in this manner only have a low stability transverse to the axial direction of the tube, since the tube sections may also inadvertently separate from one another just as they are joined together.

Bendable tubes may be manufactured considerably more simply with a method known from German published patent application DE 195 35 179 A1, in which a tube is divided into the previously described tube sections with a separation procedure, wherein an assembly of the tube section is done away with. The disadvantage with this method, however, is that one may only manufacture those tubes which, with a stable positive-fit connection of adjacent tube sections, are bendable only in a very limited manner or, with a good bending ability only have limited stability in the regions, in which adjacent tube sections are engaged with one another.

BRIEF SUMMARY OF THE INVENTION

Against this background, it is an object of the invention to provide a method for manufacturing a bendable tube with improved stability characteristics, the method being simpler and thus more economical with regard to manufacturing technology.

This object is achieved by a method for manufacturing a bendable tube in which means for producing a positive fit transversely to the axis direction of the tube are arranged peripherally at the regions of the tube sections, the regions being situated in engagement with one another.

With the method according to the invention for manufacturing a bendable tube, which is preferably envisaged for an endoscopic instrument, a tube is first separated into several tube sections in a manner such that adjacent tube sections engage into one another with a positive fit in the axis direction of the tube, and the structural integrity of the tube remains intact as far as this is concerned. Here, the separation may be effected such that the individual tube sections are separated from one another completely in a material manner. Apart from this, there is also the possibility of not completely separating the tube sections from one another, but retaining a continuous connection between the individual tube sections at a limited peripheral section. The separation of the individual tube sections from one another may be carried out with any separating method which is suitable for this, wherein the selection of the most useful separating method as the case may be depends on the material and/or the wall thickness of the tube to be fragmented. A method which is particularly suitable with thin-walled tubes and with tubes with a small tube diameter is, for example, laser cutting.

According to an embodiment of the invention, after the separation of the tube into several tube sections one envisages arranging means for producing a positive fit transverse to the axis direction of the tube, peripherally, i.e., on the outer side of the peripheral surface of the tube sections, at regions of the tube sections, which are situated in engagement with one another, wherein these means advantageously stabilize the joint connections of the individual tube sections. Here, one must typically take care to design and/or arrange these means such that a bending of the tube sections which are situated in engagement with one another, to one another, is not prevented.

Preferably, an enveloping tube, which is arranged around the bendable tube, is provided for forming the positive fit transverse to the axis direction of the bendable tube. For this, usefully the bendable tube is inserted into the enveloping tube. The use of the enveloping tube is advantageous inasmuch as all regions of the tube sections of the bendable tube, which are situated in engagement with one another, may be covered with only one component, specifically the enveloping tube, and thus may be secured or stabilized with a positive fit.

Usefully, the enveloping tube is separated into tube sections. At least a portion of the tube sections, as the case may be, however even all of these tube sections, serve for supporting the joint connections of the bendable tube, i.e., the regions of adjacent tube sections of the bendable tube, which are engaged with one another, on the outer side in the enveloping tube, in the installed state of the tube.

As a rule, it is necessary to widen the separating gap between the individual tube sections of the enveloping tube at least in the region of the side or the sides, to which the bendable tube may be bent, in order to ensure a bending of the bendable tube arranged in the enveloping tube. For this propose, the enveloping tube, for example proceeding from thin separating gaps extending over the complete periphery of the enveloping tube, between the individual tube sections, may be cut into, such that regions of the enveloping tube which widen outwardly in a wedge-like manner in the direction of the bending ability of the bendable tube, are separated away.

Apart from this, it may also be advantageous to widen the separating gap between the tube sections of the enveloping tube, such that the regions of the bendable tube, which axially border the lugs and recesses of the individual tube sections, lay completely bare. Accordingly, whole, annular sections of the enveloping tube, which in the installed position of the bendable tube in the enveloping tube do not cover the regions of the bendable tube which are situated in engagement, may be cut out, so that only narrow, annular sections of the enveloping tube, which in each case stabilize the tube sections of the bendable tube, which are situated in engagement with one another, without limiting the bending ability, are left standing radially on the outer side of the regions of the tube sections of the bendable tube, the regions being in engagement with one another.

Usefully, the division of the enveloping tube into several tube sections is effected before introducing the bendable tube into the enveloping tube. Against this background, it is particularly advantageous to design the separating gaps on dividing up the enveloping tube into the individual tube sections, in a manner such that adjacent tube sections remain connected to one another via at least one web. Accordingly, the enveloping tube for separating into the individual tube sections, is cut into, such that the separating gap arising from this is not designed in an annularly closed manner, but instead a material connection of adjacent tube sections continues to exist at least at one and preferably at several preferably narrow regions. The individual tube sections thus first form an integral component, into which the bendable tube may be introduced in a simple manner. Advantageously, the webs connecting the individual tube sections of the enveloping tube are separated and removed only after the bendable tube is arranged and positioned in this component.

Previously however, one preferably envisages welding the enveloping tube at least one web end to the bendable tube arranged therein, or connecting it in any other suitable manner. For this, the end of this web should typically be arranged on the outer side of a wall region of the bendable tube. Preferably, the enveloping tube at the ends of all webs formed on the enveloping tube is welded to the bendable tube, in order to fasten all tube sections covering the regions of the tube sections of the bendable tube, which are engaged with one another, in the position on the bendable tube which is necessary for this. For welding the web ends of the enveloping tube to the bendable tube, one may apply any welding methods which are suitable of this. Preferably, one may apply those welding connections, such as laser welding, which permit a concentrated introduction of energy into the welding location and thus only lead to a negligible shape distortion of the tube sections.

After the welding of the at least one web end on the bendable tube, it may be necessary to remove the remaining region of the web. Preferably, the webs, i.e., the web regions which do not form the material fit with the bendable tube, may however be removed already by the welding procedure creating the connection, so that an additional working step for severing and removing the webs is not necessary. This is possible, for example, if the web ends are fastened on the bendable tube by laser welding. In this case, with a suitable selection of the welding parameters, the material of the webs which does not form the material fit with the bendable tube, may be evaporated with the laser beam.

As has already been noted, it may be necessary to cut out whole, annular sections of the enveloping tube, which in the installed condition of the bendable tube in the enveloping tube do not cover the regions of the bendable tube, which are in engagement. In order to simplify the removal of these tube sections, a separating gap running essentially in the axis direction of the enveloping tube is advantageously formed on them. This separating gap permits the tube sections provided with it to break open as the case may be, or to widen so far, that they may be removed from the bendable tube transversely to the longitudinal axis of this.

In a further advantageous embodiment of the method according to the invention for manufacturing a bendable tube, one envisages in each case designing at least one separating gap between the tube sections of the bendable tube, in a manner such that these tube sections first remain connected to one another via at least one web in the regions forming the positive fit between these tube sections, and are broken open by a bending of the bendable shaft which is subsequent to this. This is advantageous inasmuch as the material connection of the individual tube sections on inserting the bendable tube into the enveloping tube still exists, and the bendable tube accordingly may be handled as an individual component in a simple manner. An advantageous auxiliary effect after the breaking of the webs is to be seen in the fact that the effective width of the previously manufactured separating gap is reduced by the web ends which then arise and which continue to remain in the separating gap between the two separate tube sections, which leads to a correspondingly smaller play in the articulated connection of the tube sections.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown in the drawings:

FIG. 7 is a longitudinal view of the bendable tube according to FIG. 1 in the completed condition;

FIG. 8 is an enlarged representation of detail D of FIG. 7;

FIG. 9 is an enlarged representation sectioned view along the section line IX-IX in FIG. 7;

DETAILED DESCRIPTION OF THE INVENTION

Figure 1:
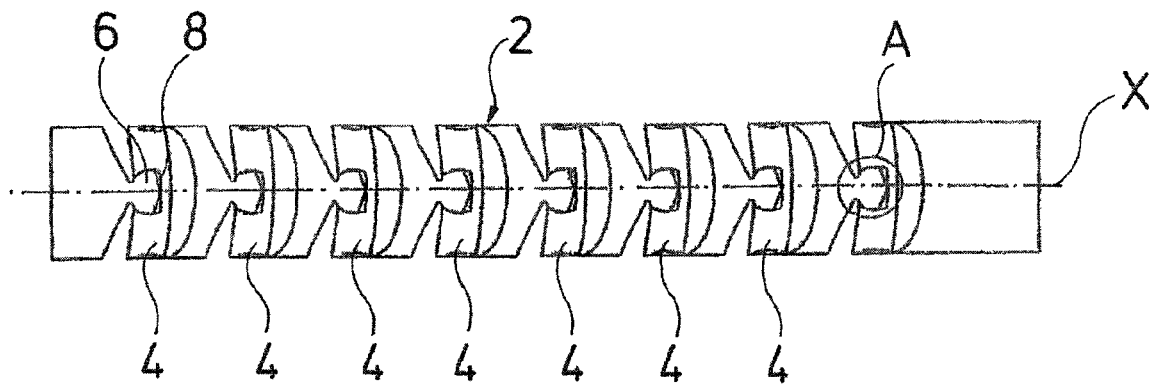
FIG. 1 is a schematic longitudinal representation of a bendable tube in a first embodiment of the invention.

For manufacturing a bendable tube, two cylindrical tubes are used with the method according to the invention. With the manufacture of a bendable tube described by way of FIGS. 1 to 9, a tube 2 is divided peripherally into several tube sections 4 with a suitable separating method, preferably laser cutting. The separating gap between adjacent tube sections 4 is designed in a manner such that a lug 6, which is aligned in a direction of the longitudinal axis of the tube 2 and which engages into a recess 8 of the adjacent tube section 4, arises on a tube section 4 at two diametrically opposite sides.

The separation of the individual tube sections 4 from one another is carried out such that the lugs 6 first widen in a circular manner in the direction of the adjacent tube section 4, into which they engage, and then taper to a blunt tip on both sides in a beveled manner. The contour of the recesses 8 which are formed on the tube sections 4 is designed such that it runs essentially normally to the longitudinal axis X at its side which lies opposite the lug 6 in the direction of a longitudinal axis X of the tube 2, and adjacent to this has a circular course which corresponds to the contour of the lug 6. In order to permit a bending of an adjacent tube section 4, the separating gap is widened in a wedge-like manner to the outside, radially on the outer side of the lugs 6. For this, additional incisions are carried out on the tube 2, by which the corresponding regions of the tube 2 are separated away.

Figure 2:
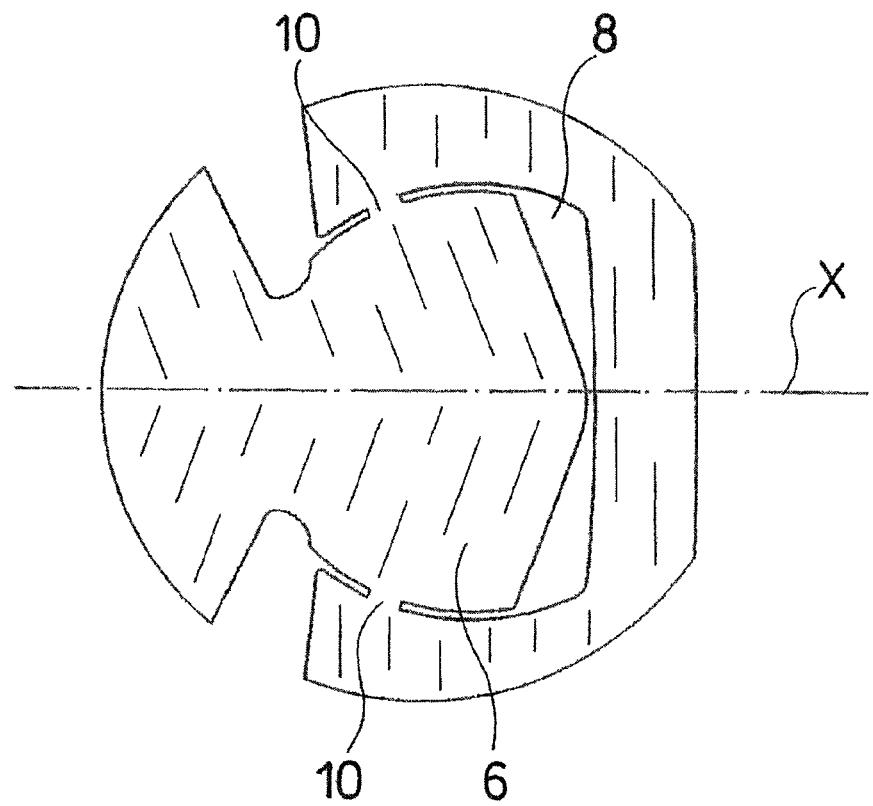
FIG. 2 is an enlarged representation of detail A of FIG. 1.
Figure 3:
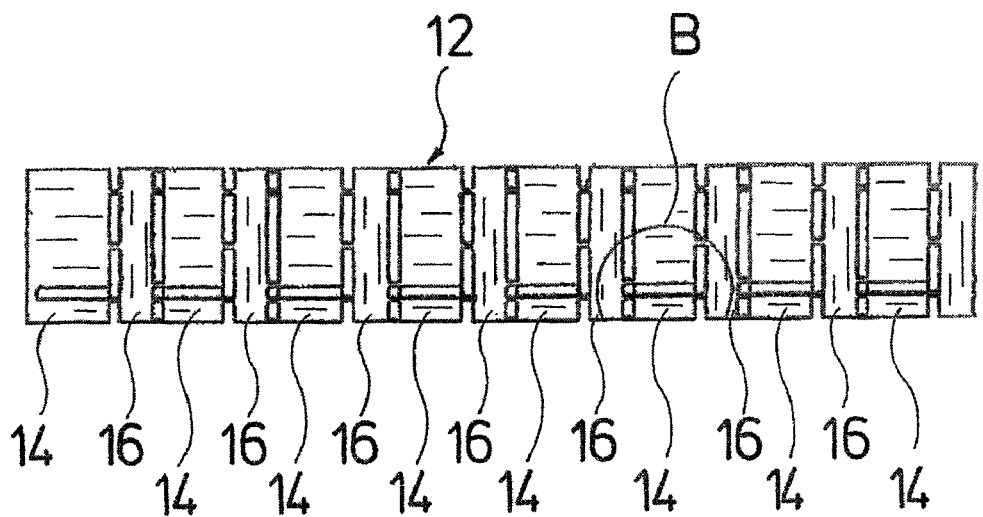
FIG. 3 is a schematic longitudinal representation of an enveloping tube according to a first embodiment of the invention.

As may be deduced from the detail A in FIG. 2, the separating gap between the adjacent sections 4 is not cut in a closed path, but interrupted in the region in which the lugs 6 engage into the recesses 8, in a manner such that the tube sections 4 remain materially connected to one another via two webs 10. Only after a severing of the webs 10, which however is only effected at a later point in time, does the tube 2 form a bendable tube 2.

The tube 2 machined in the manner described above is subsequently introduced into an enveloping tube 12. Previously however, the enveloping tube 12 is divided transversely to the longitudinal direction of the enveloping tube 12 into alternating successive tube sections 14 and 16, likewise by laser cutting, wherein the tube sections 14 and 16 differ with regard to their dimensions in the longitudinal direction of the enveloping tube 12.

Figure 4:
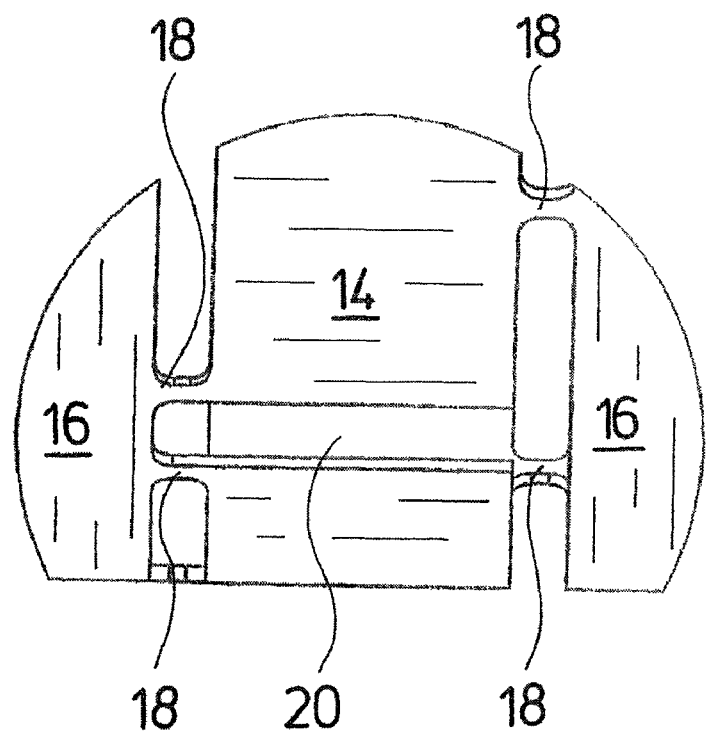
FIG. 4 is an enlarged representation of detail B of FIG. 3.
Figure 5:
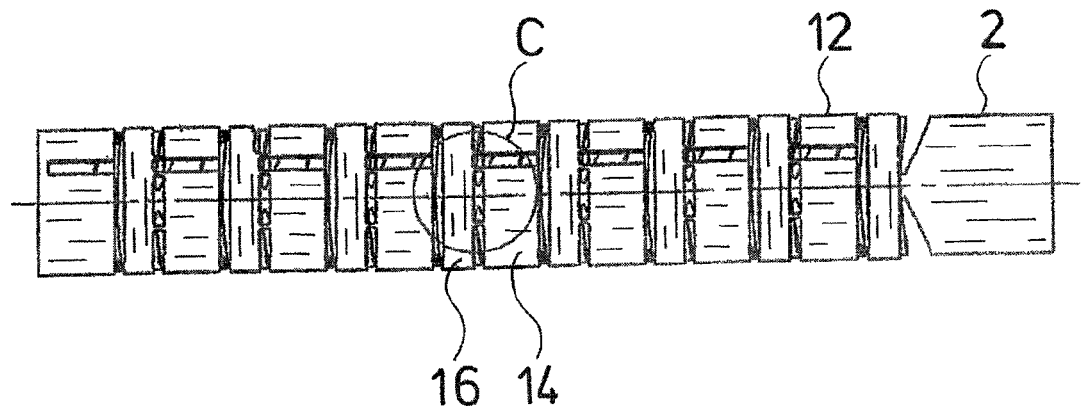
FIG. 5 is a longitudinal view of the bendable tube according to FIG. 1 in the installed condition in the enveloping tube according to FIG. 3.
Figure 6:
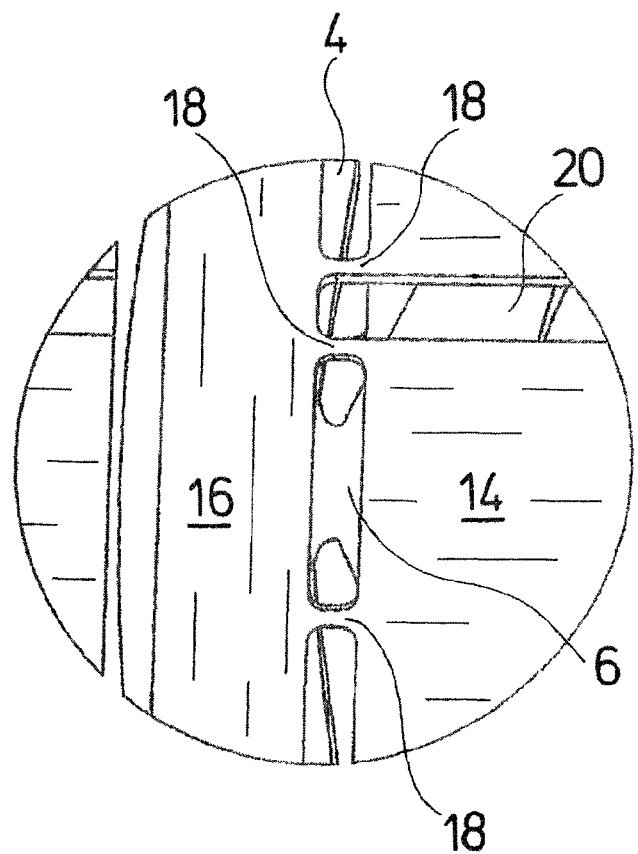
FIG. 6 is an enlarged representation of detail C of FIG. 5.
Figure 10:
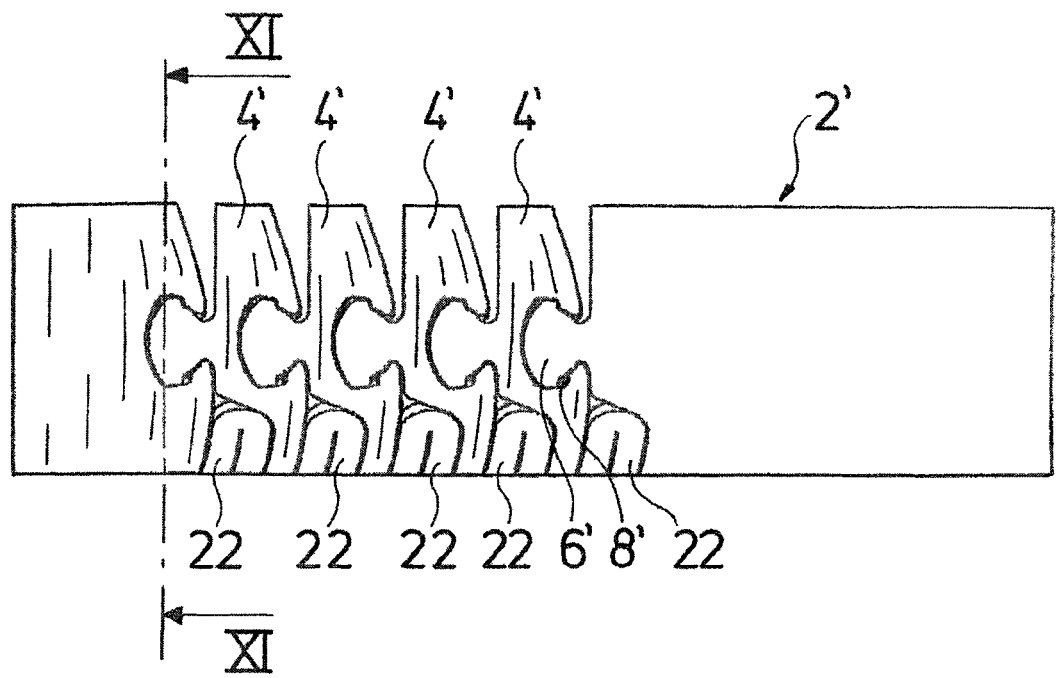
FIG. 10 is a schematic longitudinal representation of a bendable tube in a second embodiment of the invention.
Figure 11:
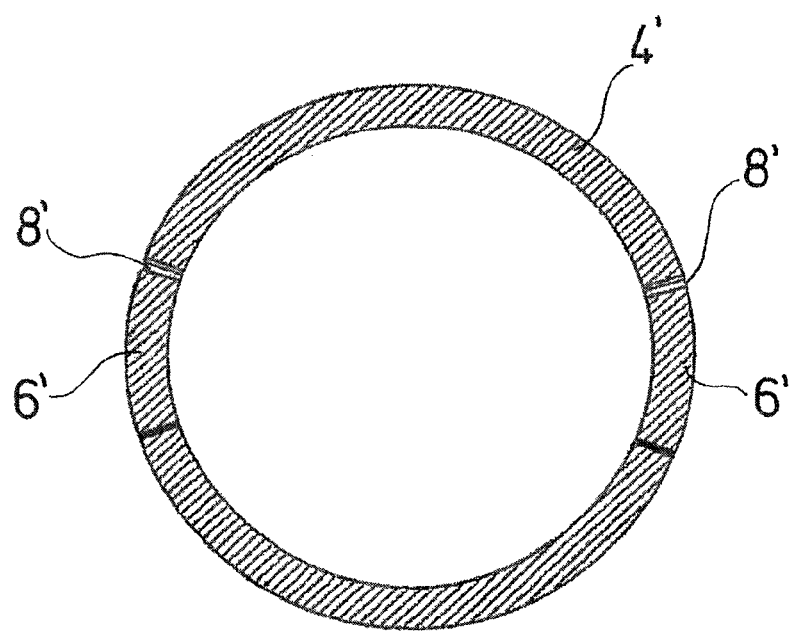
FIG. 11 is an enlarged representation sectioned view along the section line XI-XI in FIG. 10.
Figure 12:
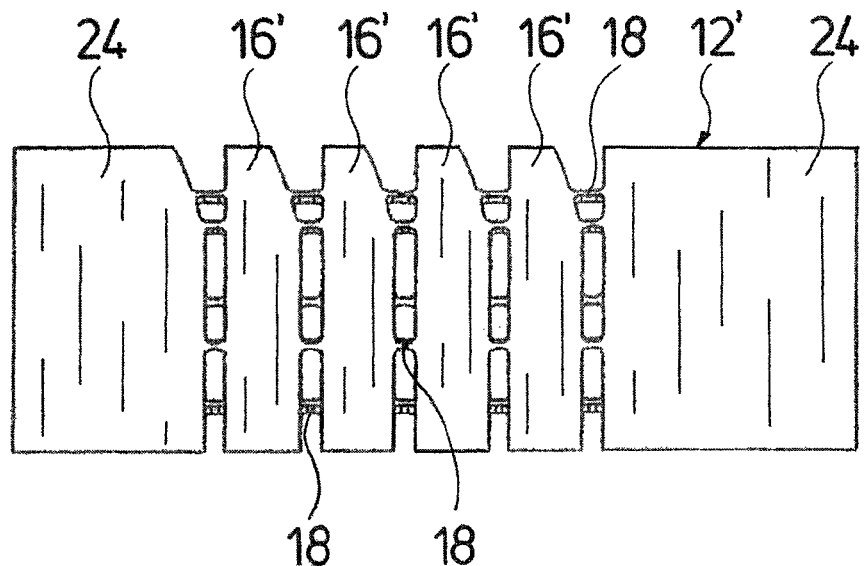
FIG. 12 is a schematic longitudinal representation of an enveloping tube according to a second embodiment.
Figure 13:
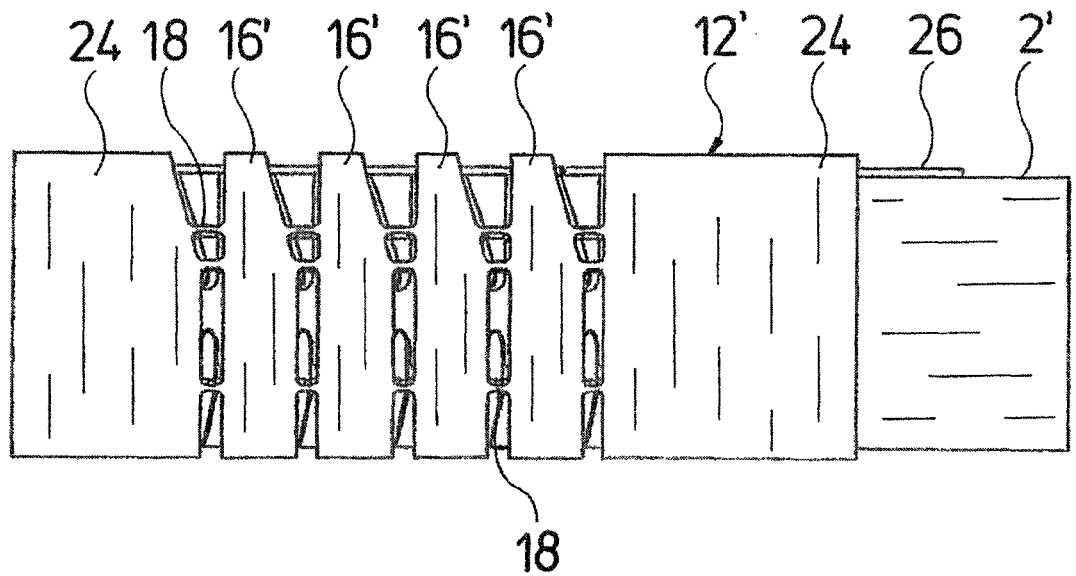
FIG. 13 is a schematic longitudinal view of the bendable tube according to FIG. 10 in the installed condition in the enveloping tube according to FIG. 12.
Figure 14:
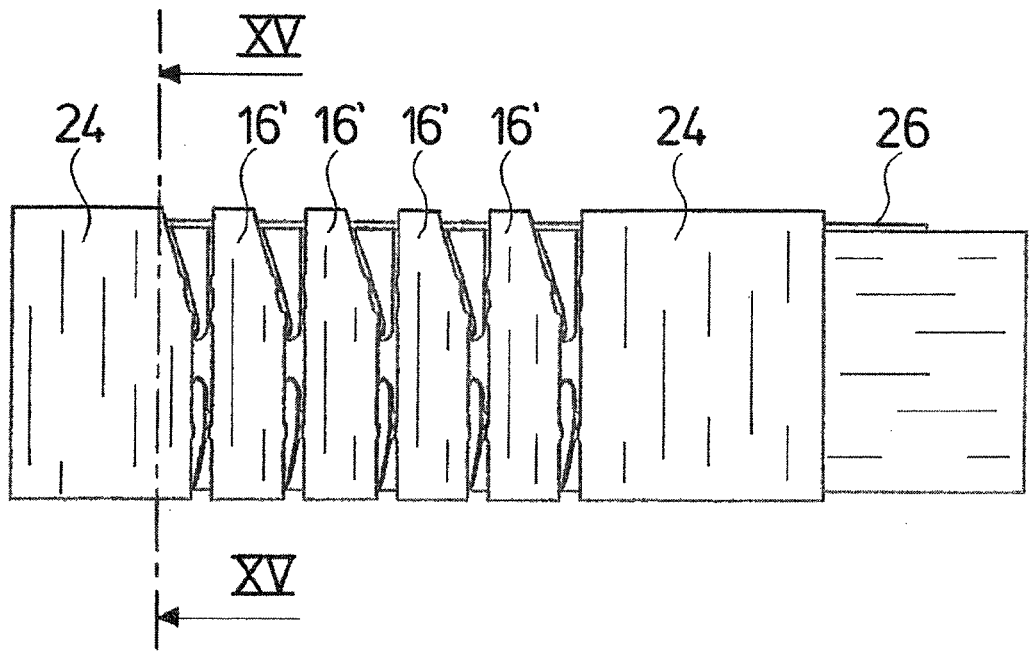
FIG. 14 is a longitudinal view of the bendable tube according to FIG. 10 in the completed condition.

As is particularly evident from FIG. 4, the tube sections 14 are not completely separated from the tube sections 16. Instead, the separating gaps between the tube sections 14 and 16 are designed in an interrupted manner, so that several webs 18 connect the tube sections 14 and 16 to one another. Moreover, the tube sections 14 are furthermore provided with a separating gap 20 which runs in the axis direction of the enveloping tube 12 and which extends over the complete length of the tube sections 14.

The tube 2 and the enveloping tube 12 are dimensioned such that the tube 2 may be inserted into the enveloping tube 12 with a small play. Here, the tube 2 is positioned in the enveloping tube 12, such that the tube sections 16 of the enveloping tube 12 in each case cover the regions of the tube 2, in which the lugs 6 engage into the recesses 8. Thereupon, the tube sections 16 of the enveloping tube 12 are welded to the tube sections 4 of the tube 2 at the edge regions which border the recess 8 (FIG. 8), wherein the regions of the webs 18, which border the tube sections 16 of the enveloping tube and which are arranged radially on the outer side of the lugs 6 formed on the tube sections 4 of the tube 2, are selected as welding locations. Moreover, the webs 18 are severed and thus the material connection of the tube sections 16 with the tube sections 14 is broken by this welding, which may be carried out with any welding method which is suitable for this.

The tube sections 14 are now movable between the tube sections 16 in the longitudinal direction of the tube 2, and are removed, wherein the separating gaps 20 simplify a breaking open or widening of the tube sections 14, which is necessary for this. Subsequently, the individual tube sections 4 are kinked relative to one another, by which the webs 10 which connect the adjacent tube sections 4, are broken open and the tube 2 obtains its bending ability. In this manner, the bendable tube 2 represented in FIG. 7 arises, with which the tube sections 16 of the enveloping tube 12 create a positive fit transverse to the axis direction of the tube 2 at the regions of the tube sections 4 of the tube 2, which are engaged with one another, and thus stabilize the tube 2.

With the manufacture of the bendable tube 2' described by way of FIGS. 10 to 15, first several tube sections 4' are likewise separated away at the tube 2'. Here, a separating gap between the tube sections 4' is also designed such that lugs 6' arise, which engage into recesses 8'. In contrast to the tube 2, the tube sections 4' of the tube 2', however, remain materially connected also in each case via a connection web 22. The tube is cut into between the individual tube sections 4' such that a connection web 22 with a meandering course arises, for forming the connection web 22. The connection web 22 obtains spring characteristics on account of its meandering course, which permits the tube 2' to be bent to the side which is distant to the connection webs 22. For this purpose, the separating gap between the individual tube sections 4' on the side of the tube 2', which is distant to the connection webs 22, is designed widened in a wedge-like manner in the radial direction.

The bendable tube 2', which is formed in such a manner, is likewise then introduced into an enveloping tube 12'. Previously, the enveloping tube is peripherally separated into several consecutive tube sections 16' which are arranged between two tube end sections 24, wherein the separating gap is designed interrupted in a manner such that webs 18 connect the individual tube sections 16. Also the separating gaps separating the tube sections 16' of the enveloping tube are designed widened to the outside in a wedge-like manner in one region by a suitable incision, corresponding to the region of the separating gap between the tube sections 4', which is widened in a wedge-like manner on the tube 2'.

The tube 2' is positioned in the enveloping tube 12' such that the tube sections 4' of the tube 2' are covered by the tube sections 16' of the enveloping tube 12'. Subsequently, the individual sections of the enveloping tube 12' are welded in the region of the webs 18 to the corresponding individual sections of the tube 2' at the edge regions which border the recess 8', wherein the webs 18 with the use of a laser welding method are further separated and removed by the welding.

Figure 15:
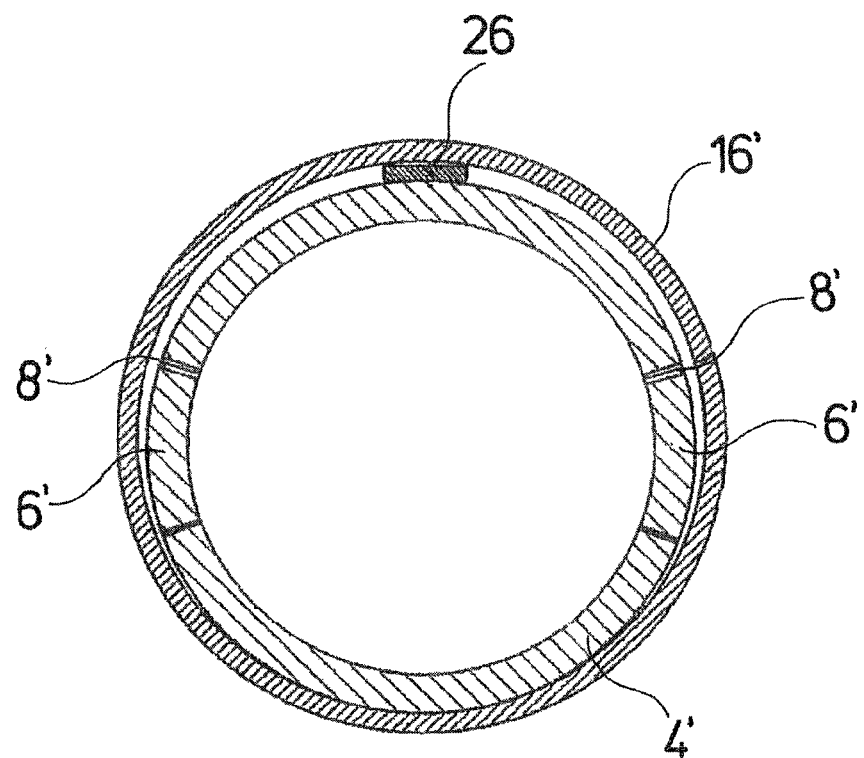
FIG. 15 is a sectioned view along the section line XV-XV in FIG. 14.

As is to be deduced from FIG. 15, the tube 2' is arranged eccentrically to the enveloping tube 12', wherein an elongate pull element 26, which is connected to the tube 2' for bending the tube 2', is arranged in the one-sided intermediate space between the tube 2' and the enveloping tube 12' which thus arises.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for manufacturing a bendable tube for an endoscopic instrument, the method comprising separating a tube (2, 2') into several tube sections (4, 4') in a manner such that adjacent tube sections (4, 4') engage into one another with a positive fit in an axis direction of the tube (2, 2'), and arranging means for forming a positive fit transverse to the axis direction of the tube (2, 2') peripherally at regions of the tube sections (4, 4'), the regions being situated in engagement with one another, wherein the means for forming the positive fit transverse to the axis direction of the tube (2, 2') comprises an enveloping tube (12) which is arranged around the tube (2, 2'), wherein the enveloping tube (12) is separated into tube sections, wherein separating gaps are formed between the tube sections of the enveloping tube (12), in such a manner that the tube sections remain connected to one another via at least one web (18), and wherein the enveloping tube (12, 12') is welded at least one web end to the bendable tube (2, 2') arranged therein.

2. The method according to claim 1, wherein the at least one web (18) is removed by the welding.

3. A method for manufacturing a bendable tube for an endoscopic instrument, the method comprising separating a tube (2, 2') into several tube sections (4, 4') in a manner such that adjacent tube sections (4, 4') engage into one another with a positive fit in an axis direction of the tube (2, 2'), and arranging means for forming a positive fit transverse to the axis direction of the tube (2, 2') peripherally at regions of the tube sections (4, 4'), the regions being situated in engagement with one another,
- wherein means for forming the positive fit transverse to the axis direction of the tube (2, 2') comprises an enveloping tube (12) which is arranged around the tube (2, 2'),
- wherein the enveloping tube (12) is separated into tube sections, and
- wherein a separating gap (20) running essentially in the axis direction of the enveloping tube (12) is formed on tube sections of the enveloping tube (12) which are to be removed.

\* \* \* \* \*